US012690880B2

(12) United States Patent (10) Patent No.: US 12,690,880 B2
Dwivedi et al. (45) Date of Patent: Jul. 28, 2026

(54) MECHANICAL THROMBECTOMY DEVICE PARTIALLY COLLAPSIBLE DURING RETRIEVAL OF AN OCCLUSION UPON ACTIVATION OF AN INTERNAL ACTUATABLE COLLAPSING MECHANISM

(71) Applicant: Neuravi Limited, Galway (IE)

(72) Inventors: Anushree Dwivedi, Galway (IE); Sarah Johnson, Galway (IE); Mahmood Mirza, Galway (IE); Joshua Khan, Galway (IE)

(73) Assignee: Neuravi Limited, Galway (IE)

( * ) Notice: Subject to any disclaimer, the term of this patent is extended or adjusted under 35 U.S.C. 154(b) by 573 days.

(21) Appl. No.: 17/816,386

(22) Filed: Jul. 29, 2022

(65) Prior Publication Data

US 2024/0032952 A1      Feb. 1, 2024

(51) Int. Cl.
*A61B 17/221* (2006.01)
*A61B 17/22* (2006.01)
(52) U.S. Cl.
CPC .. *A61B 17/221* (2013.01); *A61B 2017/22038* (2013.01); *A61B 2017/2215* (2013.01)
(58) Field of Classification Search
CPC .................. A61B 17/221; A61B 17/22; A61B 2017/22038; A61B 2017/2215; A61B 2017/2212; A61B 2017/2217; A61B 2017/320004; A61B 2017/320008; A61B 2017/22035; A61F 2/0105; A61F 2/0108; A61F 2002/016
USPC .......................................................... 606/159
See application file for complete search history.

(56) References Cited

U.S. PATENT DOCUMENTS

| | | | |
|---|---|---|---|
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |

(Continued)

OTHER PUBLICATIONS

Related, co-pending, co-owned U.S. Appl. No. 17/816,388, filed Jul. 29, 2022.

(Continued)

*Primary Examiner* — Jocelin C Tanner
(74) *Attorney, Agent, or Firm* — Troutman Pepper Locke LLP

(57) ABSTRACT

A mechanical thrombectomy device including a self-expanding cage structure transitionable from a radially expanded state to a radially partially collapsed state of reduced outer diameter relative to that while in the radially expanded state. The mechanical thrombectomy device also including an internal actuatable collapsing mechanism fixedly attached internally to the self-expanding cage structure; wherein the internal actuatable collapsing mechanism when actuated or deployed imposes a radially inward tension on the self-expanding cage structure transitioning to the radially partially collapsed state compressing the occlusion captured therein.

14 Claims, 5 Drawing Sheets

(56) References Cited

U.S. PATENT DOCUMENTS

| | | | |
|---|---|---|---|
| 9,579,484 | B2 | 2/2017 | Barnell |
| 9,585,642 | B2 | 3/2017 | Dinsmoor et al. |
| 9,615,832 | B2 | 4/2017 | Bose et al. |
| 9,615,951 | B2 | 4/2017 | Bennett et al. |
| 9,622,753 | B2 | 4/2017 | Cox |
| 9,636,115 | B2 | 5/2017 | Henry et al. |
| 9,636,439 | B2 | 5/2017 | Chu et al. |
| 9,642,675 | B2 | 5/2017 | Werneth et al. |
| 9,655,633 | B2 | 5/2017 | Leynov et al. |
| 9,655,645 | B2 | 5/2017 | Staunton |
| 9,655,989 | B2 | 5/2017 | Cruise et al. |
| 9,662,129 | B2 | 5/2017 | Galdonik et al. |
| 9,662,238 | B2 | 5/2017 | Dwork et al. |
| 9,662,425 | B2 | 5/2017 | Lilja et al. |
| 9,668,898 | B2 | 6/2017 | Wong |
| 9,675,477 | B2 | 6/2017 | Thompson |
| 9,675,782 | B2 | 6/2017 | Connolly |
| 9,676,022 | B2 | 6/2017 | Ensign et al. |
| 9,692,557 | B2 | 6/2017 | Murphy |
| 9,693,852 | B2 | 7/2017 | Lam et al. |
| 9,700,262 | B2 | 7/2017 | Janik et al. |
| 9,700,399 | B2 | 7/2017 | Acosta-Acevedo |
| 9,717,421 | B2 | 8/2017 | Griswold et al. |
| 9,717,500 | B2 | 8/2017 | Tieu et al. |
| 9,717,502 | B2 | 8/2017 | Teoh et al. |
| 9,724,103 | B2 | 8/2017 | Cruise et al. |
| 9,724,526 | B2 | 8/2017 | Strother et al. |
| 9,750,565 | B2 | 9/2017 | Bloom et al. |
| 9,757,260 | B2 | 9/2017 | Greenan |
| 9,764,111 | B2 | 9/2017 | Gulachenski |
| 9,770,251 | B2 | 9/2017 | Bowman et al. |
| 9,770,577 | B2 | 9/2017 | Li et al. |
| 9,775,621 | B2 | 10/2017 | Tompkins et al. |
| 9,775,706 | B2 | 10/2017 | Peterson et al. |
| 9,775,732 | B2 | 10/2017 | Khenansho |
| 9,788,800 | B2 | 10/2017 | Mayoras, Jr. |
| 9,795,391 | B2 | 10/2017 | Saatchi et al. |
| 9,801,980 | B2 | 10/2017 | Karino et al. |
| 9,808,599 | B2 | 11/2017 | Bowman et al. |
| 9,833,252 | B2 | 12/2017 | Sepetka et al. |
| 9,833,604 | B2 | 12/2017 | Lam et al. |
| 9,833,625 | B2 | 12/2017 | Waldhauser et al. |
| 2011/0125181 | A1 | 5/2011 | Brady et al. |
| 2014/0257362 | A1* | 9/2014 | Eidenschink ............ A61F 2/01 |
| | | | 606/200 |
| 2017/0007264 | A1 | 1/2017 | Cruise et al. |
| 2017/0007265 | A1 | 1/2017 | Guo et al. |
| 2017/0020670 | A1 | 1/2017 | Murray et al. |
| 2017/0020700 | A1 | 1/2017 | Bienvenu et al. |
| 2017/0027640 | A1 | 2/2017 | Kunis et al. |
| 2017/0027692 | A1 | 2/2017 | Bonhoeffer et al. |
| 2017/0027725 | A1 | 2/2017 | Argentine |
| 2017/0035436 | A1 | 2/2017 | Morita |
| 2017/0035567 | A1 | 2/2017 | Duffy |
| 2017/0042548 | A1 | 2/2017 | Lam |
| 2017/0049596 | A1 | 2/2017 | Schabert |
| 2017/0065299 | A1* | 3/2017 | Gillespie ................. A61F 2/962 |
| 2017/0071737 | A1 | 3/2017 | Kelley |
| 2017/0072452 | A1 | 3/2017 | Monetti et al. |
| 2017/0079671 | A1 | 3/2017 | Morero et al. |
| 2017/0079680 | A1 | 3/2017 | Bowman |
| 2017/0079766 | A1 | 3/2017 | Wang et al. |
| 2017/0079767 | A1 | 3/2017 | Leon-Yip |
| 2017/0079812 | A1 | 3/2017 | Lam et al. |
| 2017/0079817 | A1 | 3/2017 | Sepetka et al. |

| | | | |
|---|---|---|---|
| 2017/0079819 | A1 | 3/2017 | Pung et al. |
| 2017/0079820 | A1 | 3/2017 | Lam et al. |
| 2017/0086851 | A1 | 3/2017 | Wallace et al. |
| 2017/0086996 | A1 | 3/2017 | Peterson et al. |
| 2017/0095259 | A1 | 4/2017 | Tompkins et al. |
| 2017/0100126 | A1 | 4/2017 | Bowman et al. |
| 2017/0100141 | A1 | 4/2017 | Morero et al. |
| 2017/0100143 | A1 | 4/2017 | Grandfield |
| 2017/0100183 | A1 | 4/2017 | Iaizzo et al. |
| 2017/0113023 | A1 | 4/2017 | Steingisser et al. |
| 2017/0147765 | A1 | 5/2017 | Mehta |
| 2017/0151032 | A1 | 6/2017 | Loisel |
| 2017/0165062 | A1 | 6/2017 | Rothstein |
| 2017/0165065 | A1 | 6/2017 | Rothstein et al. |
| 2017/0165454 | A1 | 6/2017 | Tuohy et al. |
| 2017/0172581 | A1 | 6/2017 | Bose et al. |
| 2017/0172766 | A1 | 6/2017 | Vong et al. |
| 2017/0172772 | A1 | 6/2017 | Khenansho |
| 2017/0189033 | A1 | 7/2017 | Sepetka et al. |
| 2017/0189035 | A1 | 7/2017 | Porter |
| 2017/0215902 | A1 | 8/2017 | Leynov et al. |
| 2017/0216484 | A1 | 8/2017 | Cruise et al. |
| 2017/0224350 | A1 | 8/2017 | Shimizu et al. |
| 2017/0224355 | A1 | 8/2017 | Bowman et al. |
| 2017/0224467 | A1 | 8/2017 | Piccagli et al. |
| 2017/0224511 | A1 | 8/2017 | Dwork et al. |
| 2017/0224953 | A1 | 8/2017 | Tran et al. |
| 2017/0231749 | A1 | 8/2017 | Perkins et al. |
| 2017/0252064 | A1 | 9/2017 | Staunton |
| 2017/0265983 | A1 | 9/2017 | Lam et al. |
| 2017/0281192 | A1 | 10/2017 | Tieu et al. |
| 2017/0281331 | A1 | 10/2017 | Perkins et al. |
| 2017/0281344 | A1 | 10/2017 | Costello |
| 2017/0281909 | A1 | 10/2017 | Northrop et al. |
| 2017/0281912 | A1 | 10/2017 | Melder et al. |
| 2017/0290593 | A1 | 10/2017 | Cruise et al. |
| 2017/0290654 | A1 | 10/2017 | Sethna |
| 2017/0296324 | A1 | 10/2017 | Argentine |
| 2017/0296325 | A1 | 10/2017 | Marrocco et al. |
| 2017/0303939 | A1 | 10/2017 | Greenhalgh et al. |
| 2017/0303942 | A1 | 10/2017 | Greenhalgh et al. |
| 2017/0303947 | A1 | 10/2017 | Greenhalgh et al. |
| 2017/0303948 | A1 | 10/2017 | Wallace et al. |
| 2017/0304041 | A1 | 10/2017 | Argentine |
| 2017/0304097 | A1 | 10/2017 | Corwin et al. |
| 2017/0304595 | A1 | 10/2017 | Nagasrinivasa et al. |
| 2017/0312109 | A1 | 11/2017 | Le |
| 2017/0312484 | A1 | 11/2017 | Shipley et al. |
| 2017/0316561 | A1 | 11/2017 | Helm et al. |
| 2017/0319826 | A1 | 11/2017 | Bowman et al. |
| 2017/0333228 | A1 | 11/2017 | Orth et al. |
| 2017/0333236 | A1 | 11/2017 | Greenan |
| 2017/0333678 | A1 | 11/2017 | Bowman et al. |
| 2017/0340383 | A1 | 11/2017 | Bloom et al. |
| 2017/0348014 | A1 | 12/2017 | Wallace et al. |
| 2017/0348514 | A1 | 12/2017 | Guyon et al. |
| 2019/0000492 | A1 | 1/2019 | Casey et al. |
| 2022/0202428 | A1 | 6/2022 | Lee |

OTHER PUBLICATIONS

Gupta et al., "New Class of Radial Adjustable Stentrivers for Acute Ischemic stroke", Stroke, vol. 52, pp. 1534-1544 (May 2021).
International Search Report dated Nov. 14, 2023, in corresponding International Application No. PCT/EP2023/070986, and submitted herewith.

* cited by examiner

D
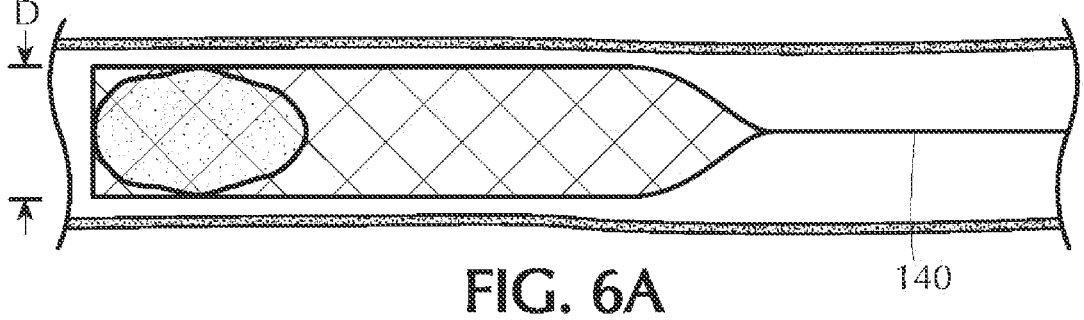
FIG. 6A     140
d
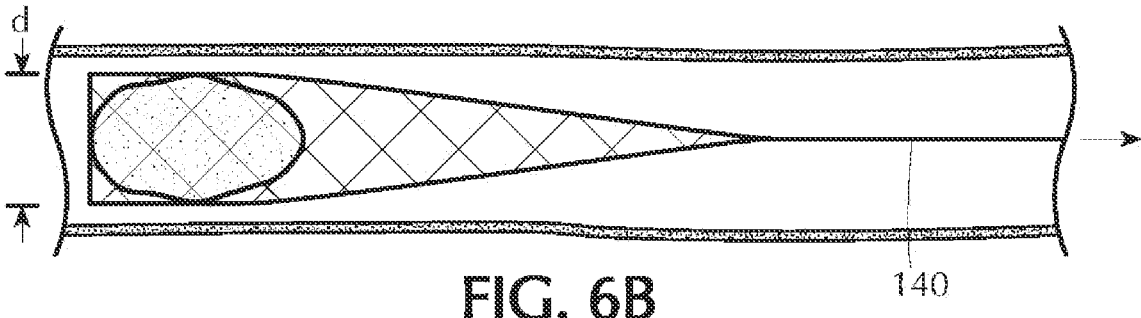
FIG. 6B     140

MECHANICAL THROMBECTOMY DEVICE PARTIALLY COLLAPSIBLE DURING RETRIEVAL OF AN OCCLUSION UPON ACTIVATION OF AN INTERNAL ACTUATABLE COLLAPSING MECHANISM

FIELD OF THE INVENTION

The present invention relates to a mechanical thrombectomy device used in intravascular treatment procedures (e.g., during a thrombectomy procedure to remove a clot). In particular, the present invention is directed to a mechanical thrombectomy device that is radially partially collapsible (i.e., reduced in outer diameter/outer profile) in response to activation of an internal actuatable collapsing mechanism following capture of the occlusion therein making it particularly well suited for retrieval of occlusions located in distal vessels.

DESCRIPTION OF RELATED ART

Arteries or vessels in the brain may become occluded resulting in acute ischemic stroke (AIS). Endovascular treatment procedures or therapies include use of a mechanical thrombectomy device (e.g., stentriever) navigated through the vasculature to capture and retrieve the target occlusion. Occlusions may be identified in various areas of the vasculature, for example, in the brain. One type of cerebral occlusions (commonly referred to as large-vessel occlusions (LVOs) or proximal occlusions) are located in one of the major arteries of the anatomy of the brain (e.g., Internal Carotid Artery (ICA), ICA terminus (TT-lesion; T occlusion). Middle Cerebral Artery (MCA), M1 MCA, Vertebral Artery, or Basilar Artery). An alternatively used term for large-vessel occlusions are proximal occlusions in which the name refers to the fact that these types of blockages are disposed in the vasculature of the brain proximally relative to other types of blockages located distally of one of the major arteries of the anatomy of the brain and thus referred to as distal occlusions. Distal occlusions often arise from unintended debris/fragmentation and/or escape from retrieval devices (e.g., stentrievers) during manipulation of an original/primary occlusion located more proximal relative thereto.

To achieve maximum benefits, capture of such distal occlusion and recanalization of these distal vessels is desirable, however, current mechanical thrombectomy devices exhibit several drawbacks and pose significant health risks. Additional challenges are at play when treating occlusion located in distal vessels of the brain. One aspect is that distal vessels are often very tortuous and require longer devices to access, which in turn increases the difficulty of navigating and tracking catheters to these location as they often lose pushability. Additionally, the tissue surrounding these vessels is delicate/fragile and brain structures are subject to possible significant movement during retrieval. Occlusions in these distal vessels are typically treated using conventional mechanical thrombectomy devices (e.g., conventional stentrievers). A substantial risk of damaging the blood vessels, rupture or perforators, vasospasm and even hemorrhage arises when using a conventional mechanical thrombectomy device (e.g., conventional stentriever) in the capture and retrieval of an occlusion located in a distal vessel. Another disadvantage with use of conventional mechanical thrombectomy devices in treating occlusions in distal vessels is the risk of dislodgement of the captured clot during retrieval.

It would be desirable to develop an improved mechanical thrombectomy device that reduces these risks thereby improving overall outcome. Furthermore, it would be desirable to develop an improved mechanical thrombectomy device having a tightened grip on the captured clot thereby minimizing the risk of unintentional release while navigating the tortuous pathway of the distal vessels while simultaneously minimizing the friction force imparted on the fragile blood vessel wall and associated risk of complications due to bleeding.

SUMMARY OF THE INVENTION

An aspect of the present invention is directed to an improved mechanical thrombectomy device that during retrieval of a clot captured therein minimizes friction or drag with the vessel wall and thus minimizes the potential risk of damage/rupture thereto.

Another aspect of the present invention relates to an improved mechanical thrombectomy device including an internal actuatable collapsing mechanism that when actuated (i.e., under tension subject to application of a force in a proximal direction (e.g., pulling in a proximal direction on a pull wire)) causes the self-expanding cage structure of the mechanical thrombectomy device to radially partially collapse (i.e., reduce in outer diameter/outer profile relative to that while in a radially expanded state prior to actuation of the internal actuatable collapsing mechanism) prior to reverting/being drawn back into the microcatheter/catheter.

While another aspect of the present invention relates to an improved mechanical thrombectomy device that when radially partially collapsed pinches/clamps down on the clot captured therein thereby minimizing the potential risk of loosening its grip (i.e., dislodgement) when navigated through the tortuous vessel pathway during retrieval from the body.

Still another aspect of the invention is directed to a mechanical thrombectomy device including a self-expanding cage structure transitionable from a radially expanded state to a radially partially collapsed state of reduced outer diameter relative to that while in the radially expanded state. The mechanical thrombectomy device also including an internal actuatable collapsing mechanism fixedly attached internally to the self-expanding cage structure; wherein the internal actuatable collapsing mechanism when actuated imposes a radially inward tension on the self-expanding cage structure transitioning to the radially partially collapsed state.

Yet another aspect of the invention is directed to a method for capture and retrieval of an occlusion in a vessel using a mechanical thrombectomy device as described in the preceding paragraph. A guidewire is inserted though the vessel to a proximal side of the occlusion. Next, a microcatheter is tracked over the guidewire to the proximal side of the occlusion. Together or independently one-after-the other, the guidewire and microcatheter are advanced through the occlusion. Then the guidewire is withdrawn from the vessel. At this point the mechanical thrombectomy device is advanced through the microcatheter, whereafter the mechanical thrombectomy device is actuated thereby transitioning to the radially expanded state and capturing the occlusion therein. By imposing a radially inward tension internally within the self-expanding cage structure, the internal actuatable collapsing mechanism is deployed thereby transitioning from the radially expanded state to the radially partially collapsed state reduced in outer diameter while compressing the occlusion captured therein. With the compressed occlusion captured therein, the self-expanding cage structure is drawn back into the microcatheter while in in the radially partially collapsed state.

BRIEF DESCRIPTION OF THE DRAWING

The foregoing and other features of the present invention will be more readily apparent from the following detailed description and drawings illustrative of the invention wherein like reference numbers refer to similar elements throughout the several views and in which:

FIG. 6A is a side view of the present inventive mechanical thrombectomy device with a clot capture therein prior to actuating the internal actuatable collapsing mechanism; and FIG. 6B is a side view of the mechanical thrombectomy device of FIG. 6A after actuating the internal actuatable collapsing mechanism illustrating a portion of the mechanical thrombectomy device coinciding (e.g., aligned) with the clot having a smaller reduction in outer diameter than that portion of the mechanical thrombectomy device that does not.

DETAILED DESCRIPTION OF THE INVENTION

In the description, the terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionist. The terms "occlusion", "clot" or "blockage" are used interchangeably.

The present inventive internal actuatable collapsing mechanism is usable with any desired design or configuration of a mechanical thrombectomy device. In an exemplary configuration of the mechanical thrombectomy device designed as a plurality of articulated scaffolding sections (i.e., cells) the number of articulated scaffolding sections (i.e., cells) as well as the particular arrangement/design of the struts associated with each scaffolding section (i.e., cell) may be selected, as desired, and may differ or be the same for each scaffolding section. Furthermore, the present inventive internal actuatable collapsing mechanism may be employed with a dual structure mechanical thrombectomy device of multiple self-expanding cage structures nested together deliverable to a target sit as a single assembled unit but independently actuatable of one another. For instance, the dual structure mechanical thrombectomy device may be configured to include at least one inner self-expanding cage structure nested within an axial/longitudinal channel of an outermost self-expanding cage structure, wherein each self-expanding cage structure is independently actuatable of one another.

Figure 1A:
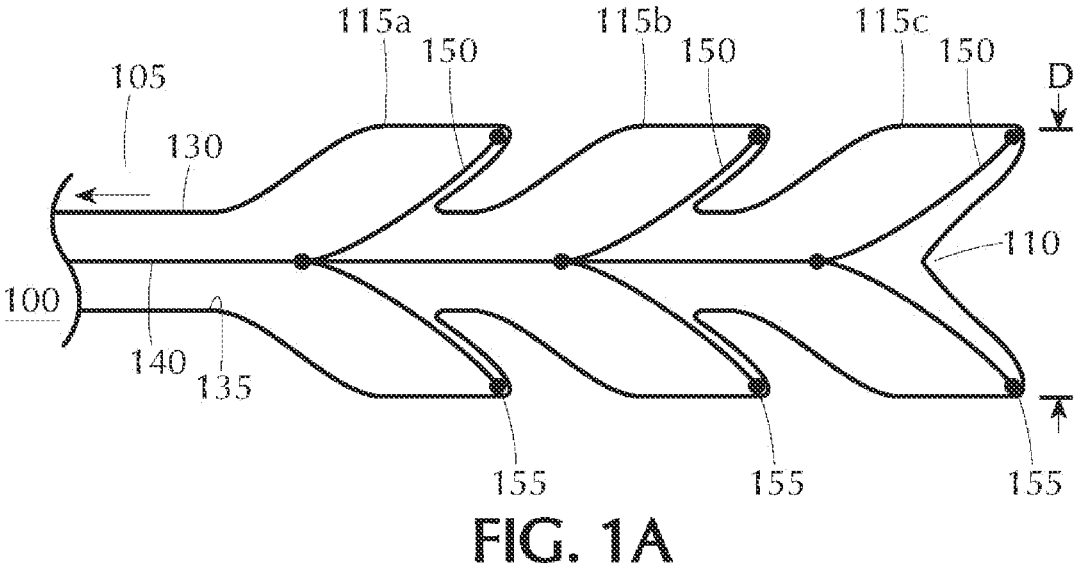
FIG. 1A is a side view of an exemplary mechanical thrombectomy device with an internal actuatable collapsing mechanism (e.g., pull wire) in accordance with the present invention; wherein the mechanical thrombectomy device is depicted in a radially expanded state prior to actuating the internal actuatable collapsing mechanism.
Figure 1B:
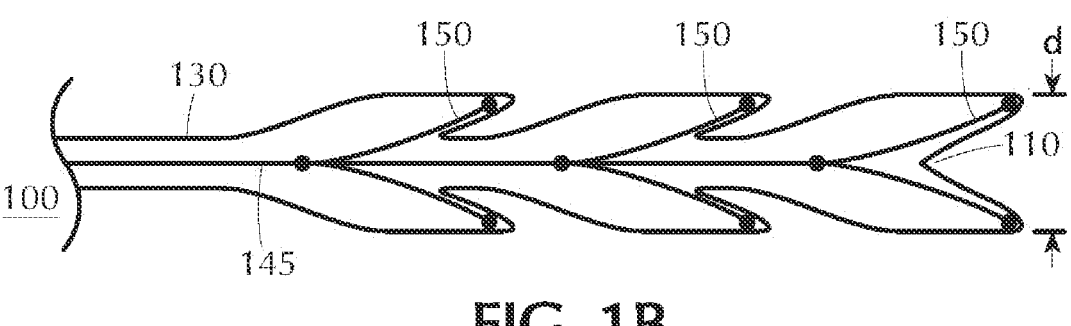
FIG. 1B is a side view of the exemplary mechanical thrombectomy device of FIG. 1A depicted in a radially partially collapsed state (i.e., reduced in outer diameter/outer profile relative to that in the radially expanded state of FIG. 1A) as a result of actuating the internal actuatable collapsing mechanism.

By way of example, the present inventive mechanical thrombectomy device is illustrated and described herein as three articulated scaffolding sections. FIG. 1A is a side view of an example mechanical thrombectomy device 100 in accordance with the present invention in a radially expanded state having an outer diameter/outer profile "D" prior to actuation/deployment of an internal actuatable collapsing mechanism (depicted in a non-actuated/non-deployed state). The same mechanical thrombectomy device is depicted in FIG. 1B following actuation/deployment of the internal actuatable collapsing mechanism (depicted in an actuated/deployed state) resulting in the mechanical thrombectomy device in a radially partially collapsed state (i.e., having a radial outer profile/outer diameter "d", wherein "d"<"D"). FIGS. 1A & 1B provide a clear visualization of the internal actuatable collapsing mechanism and its connection points internally to each articulated scaffolding section comprising the self-expanding cage structure of the mechanical thrombectomy device.

As previously noted, the mechanical thrombectomy device illustrated and described herein has an articulated design that includes three scaffolding sections 115a, 115, 115c (i.e., three cells) arranged in series one after the other in an axial/longitudinal direction from a proximal end 105 to an opposite distal end 110. Specifically, the distal end of the first scaffolding section 115a is connected or attached to the proximal end of the second scaffolding section 115*b*, while the distal end of the second scaffolding section 115*b* is connected or attached to the proximal end of the third scaffolding section 115*c*. Each scaffolding section 115*a*, 115*b*, 115*c* in all of the example mechanical thrombectomy devices illustrated and described herein are identical in configuration, but need not necessarily be so. The configuration and number of struts or arms for each scaffolding section may be the same or different for any particular mechanical thrombectomy device. First scaffolding section 115*a* is connected at its proximal end to a proximal shaft 130 (e.g., tube) having a channel 135 defined in an axial/longitudinal direction therethrough.

Conventional self-expanding mechanical thrombectomy devices are compressed or collapsed (reduced in outer profile or outer diameter) during retrieval in a proximal direction of the captured clot only when subject to application of an external compression force imposed radially inward (i.e., when reverting/returning/drawn back into the distal end of the microcatheter/catheter). Specifically, when unsheathed from the microcatheter, the conventional mechanical thrombectomy device is in an expanded state having an outer diameter/outer profile greater than the inner diameter lumen of the microcatheter. Accordingly, it is only when the conventional mechanical thrombectomy device is drawn back into the smaller inner diameter lumen of the microcatheter that an external force is imposed radially inward compressing (i.e., reducing in outer diameter/outer profile) the self-expanding cage structure. Whereas, radially partial collapse (i.e., reduction in outer profile or outer diameter) of the present inventive mechanical thrombectomy device may be realized exclusively by actuation of an internal actuatable collapsing mechanism at any desired location or time (e.g., prior to being retrieved (i.e., pulled back in a proximal direction) into the microcatheter). In other words, during retrieval or withdraw of the captured clot prior to being drawn back into the microcatheter, the mechanical thrombectomy device may be radially partially collapsed (i.e., reduced in outer diameter or outer profile) when subject to an internal tension force as the internal collapsing mechanism is pulled in a proximal direction.

Accordingly, the partial collapse of the prevent inventive mechanical thrombectomy device may be achieved solely by application of an internal tension on the cage structure (i.e., devoid or free from application of an external compression force applied radially inward on the outer surface of the self-expanding cage structure during retrieval into the microcatheter). Furthermore, radially partial collapse of the present inventive mechanical thrombectomy device resulting from actuation of the internal actuatable collapsing mechanism advantageously may occur at the location of capture of the clot in the vessel prior to being withdrawn into (i.e., distally of) the microcatheter. Thus, at the onset of retrieval of the captured clot (at a location distally of the distal end of the microcatheter) the mechanical thrombectomy device may be radially partially collapsed reducing its outer diameter diminishing friction or drag on the vessel wall thereby minimizing risk of damage or rupture to vessels.

The exemplary internal actuatable collapsing mechanism depicted in the drawings and described herein is a pull wire 140 threaded through the channel 135 of the proximal shaft 130. A proximal end of the pull wire 140 extends in a proximal direction through the microcatheter externally of the body able to be easily manipulated (e.g., pulled in a proximal direction) by the interventionalist. Pull wire 140 has an axial/longitudinal main section 145 and one or more branch sections 150 (e.g., offshoot, fingers) extending out from the main section 145 into an open interior space defined by each scaffolding section 115*a*, 115*b*, 115*c*. Main and branch sections 145, 150 comprising pull wire 140 are depicted as a single integral unit laser cut in a desired configuration from a single piece of material, but may otherwise comprise multiple units or sections adhered, laser welded or otherwise fixedly secured together as a single unit. A distal end/tip of each branch section 150 is fixedly attached (e.g., adhered or welded) internally to an associated scaffolding section 115*a*, 115*b*, 115*c* at a connection point 155. Once again, the number of branch sections 150 and connection point thereof at a particular location to each scaffolding section 115*a*, 115*b*, 115*c* may be modified, as desired. In the example depicted in the drawings, each scaffolding section 115*a*, 115*b*, 115*c* has a single corresponding or associated branch section 150. However, every scaffolding section 115*a*, 115*b*, 115*c* may have more than one associated branch section 150 connected thereto or none at all. Rather, branch sections 150 may be employed, as desired, for all, some, periodic (e.g., every other one, every second one, etc.) or random selection of scaffolding sections.

Furthermore, the extent, degree or amount of radially partial collapse (i.e., extent of reduction in outer diameter/outer profile) of the present inventive mechanical thrombectomy device may be controlled depending on the axial/longitudinal displacement (e.g., pulling) of the pull wire in a proximal direction by the interventionalist. The greater the tension (i.e., larger the displacement in an axial/longitudinal direction) imposed on the pull wire the greater the radially partial collapse (i.e., larger reduction in outer diameter) of the mechanical thrombectomy device, whereas the lesser the tension (i.e., smaller the displacement in the axial/longitudinal direction) imposed on the pull wire the lesser the radially partial collapse (i.e., smaller the reduction in outer diameter of the mechanical thrombectomy device). There being a direct relationship between the tension (i.e., the amount of displacement in the axial/longitudinal direction) applied to the pull wire and the extent/degree of the radially partial collapse (i.e., the amount by which the outer diameter of the mechanical thrombectomy device is compressed or reduced).

If desired, sufficient force (i.e., greater tension) may be imposed on the pull wire so that when radially partially collapsed the mechanical thrombectomy device has a reduced outer diameter that is less than or equal to the inner diameter of the lumen of the microcatheter. In this situation, no external compressive force radially inward would be imparted whatsoever on the radially partially collapsed mechanical thrombectomy device when drawn back into the microcatheter. Alternatively, it is also contemplated that a smaller force (i.e., lesser tension or smaller axial/longitudinal displacement) may be imposed on the pull wire so that the reduced outer diameter of the radially partially collapsed mechanical thrombectomy device is nevertheless greater than the inner diameter of the lumen of the microcatheter. With this alternative design, during retrieval when drawn back into the microcatheter an external compressive force radially inward will be imparted on the partially collapsed mechanical thrombectomy device further reducing its outer profile.

Figure 5:
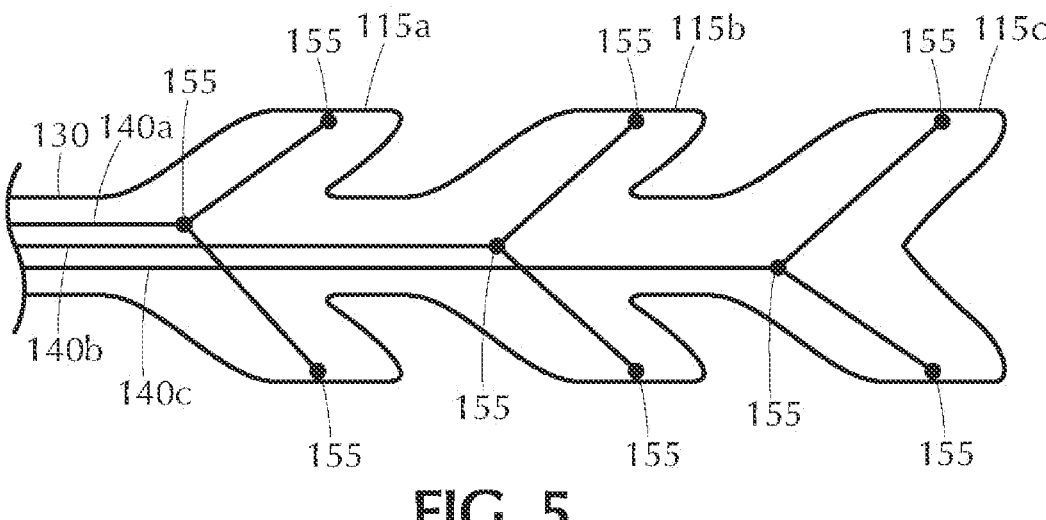
FIG. 5 is a side view of yet another exemplary mechanical thrombectomy device having three internal actuatable collapsing mechanisms (e.g., three separate pull wires each independently actuatable of one another) internally connected to a different one of the articulated scaffolding sections; wherein the mechanical thrombectomy device is depicted in a radially expanded state prior to actuating any of the three internal actuatable collapsing mechanisms.

Since all branch sections 150 in the exemplary configuration shown in FIGS. 1A & 1B are connected to the main section 145 forming an integral single unit, pulling in a proximal direction on the proximal end of the single pull wire 140 results in the simultaneous radially partial collapse of all the scaffolding sections 115*a*, 115*b*, 115*c*. However, it is further contemplated that more than one pull wire may be provided wherein each pull wire may be actuated or deployed independently of one another to radially partially collapse each or some of the scaffolding sections at different times (e.g., sequentially one after the other) rather than simultaneously. For instance, the internal actuatable collapsing mechanism may comprise three pull wires 140*a*, 140*b*, 140*c* each separate and independently actuatable from one another, as shown in FIG. 5. A first pull wire 140*a* is connected or attached internally to the first scaffolding section 115*a*; a second pull wire 140*b* is connected or attached internally to the second scaffolding section 115*b*; and a third pull wire 140*c* is connected or attached internally to the third outer cage scaffolding section 115*c*. The timing and extent of collapse of each scaffolding section 115*a*, 115*b*, 115*c* may therefore be independently actuated and controlled via pulling on the respective pull wires 140*a*, 140*b*, 140*c*. Independent actuation of each of the respective pull wires 140*a*, 140*b*, 140*c* may be sequentially (i.e., one after the other), randomly, or perhaps some, but not all, being actuated at the same time. Moreover, it is also possible in use that one or more pull wire(s) associated with a particular articulated scaffolding section never be actuated. The internal actuatable collapsing mechanism may configured to include any number of one or more pull wires connected to one or more scaffolding sections with the timing and/or decision whether to actuate each pull wire independently controllable, as desired.

In the case of multiple pull wires, each pull wire may be actuated or deployed independently of one another in order to control the extent, degree or amount of radially partial collapse (i.e., the extent, degree or amount of reduction in outer diameter or outer profile) of an associated articulated scaffolding section depending on the extent, degree or amount of tension (i.e., displacement in an axial/longitudinal direction) imposed on that particular pull wire. That is, the greater the axial/linear displacement in a proximal direction on the pull wire (i.e., the greater the tension imposed) the greater the radially partial collapse (i.e., the larger the radial reduction in outer profile/outer diameter) of the scaffolding section to which the pull wire is connected. Accordingly, the extent, degree or amount of radial reduction of each scaffolding section may be independently controlled by manipulating its associated pull wire internally connected thereto.

Moreover, in view of the fact that the extent, degree or amount of radially partial collapse may be controlled based on the axial/longitudinal displacement of (i.e., tension imparted on) the pull wire, following capture of the clot the extent, degree or amount of tension (i.e., axial/longitudinal displacement) imposed on any single pull wire may also be varied in multiple stages depending on the position or location of the mechanical thrombectomy device and captured clot therein while navigating through the vessel during retrieval. For instance, with the mechanical thrombectomy device positioned in the vessel at a location in which the clot is captured therein, a first stage of axial/longitudinal displacement (i.e., a first predetermined tension) may be imposed in a proximal direction on the pull wire resulting in an initial radially partial collapse (e.g., an initial reduction in outer diameter). As the tortuous vasculature is navigated, upon reaching the distal end/tip of the microcatheter, the mechanical thrombectomy device may undergo a further radially partial collapse (i.e., further reduction in outer diameter relative to the initial reduction in outer diameter) actuated by imposing a second stage of axial/longitudinal displacement greater than the first stage of axial/longitudinal displacement (i.e., a second predetermined tension greater than the first predetermined tension) on the same pull wire. This multi-stage collapse (e.g., two-stage collapse) by varying the tension imparted on the same pull wire at different positions or locations of the mechanical thrombectomy device within the vessel ensures that during retrieval when the mechanical thrombectomy device is drawn back into the microcatheter the clot embedded therein does not dislodge.

Accordingly, the number of pull wires as well as the independent control of each pull wire (i.e., timing of actuation of each pull wire and/or the extent, degree or amount of tension applied to each pull wire) may be varied, as desired.

Figure 2A:
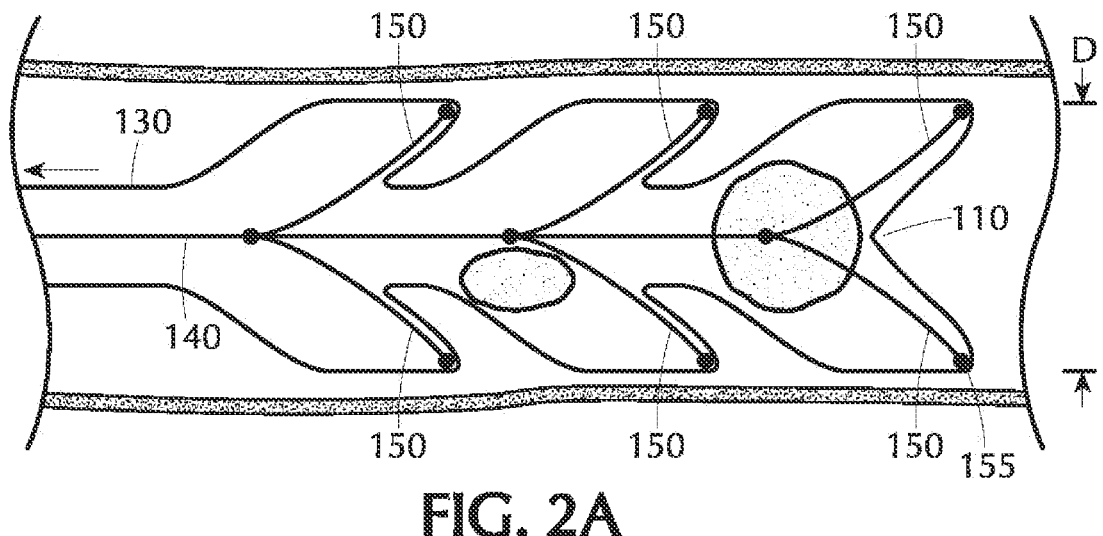
FIG. 2A is a side view of the exemplary mechanical thrombectomy device of FIG. 1A with two clots embedded therein; wherein the mechanical thrombectomy device is depicted in a radially expanded state prior to actuating the internal actuatable collapsing mechanism.
Figure 4:
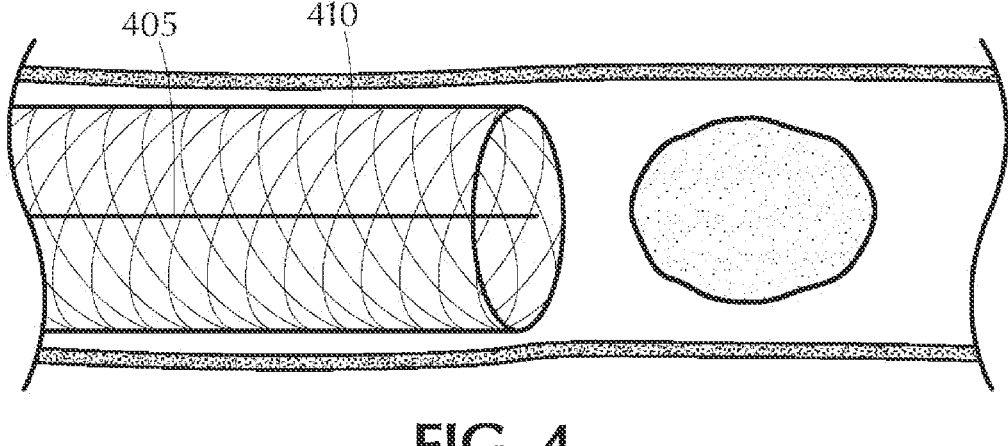
FIG. 4 depicts preliminary steps in the endovascular treatment or procedure in accordance with any of the configurations of the present invention in which a guidewire is initially navigated to a target site in the vessel followed thereafter by a microcatheter tracked over the guidewire.

In operation, a guidewire 405 is navigated through the vessel to the proximal face of a target clot. Thereafter, a microcatheter 410 is tracked over the guidewire 405 to the proximal face of the target clot, as shown in FIG. 4. The microcatheter 410 together with the guidewire 405 disposed in the lumen thereof traverses the target clot. Thereafter, the guidewire 405 is withdrawn in a proximal direction from the microcatheter 410 and the present inventive mechanical thrombectomy device is advanced in a distal direction through the lumen of the microcatheter 410 spanning the target clot. The microcatheter 410 is then withdrawn in a proximal direction whereby the unsheathed mechanical thrombectomy device self-expands radially to an outer profile or outer diameter "D" capturing the target clot therein, as illustrated in FIG. 2A. Next, the internal actuatable collapsing mechanism is actuated or deployed by the interventionalist pulling on the proximal end of the pull wire 140 in a proximal direction (as denoted by the arrow in FIG. 2B). In so doing, those scaffolding sections 115*a*, 115*b*, 115*c* having an associated branch section 150 attached to the pull wire 140 via the connection point 155 radially partially collapse (i.e., reduce in outer profile or outer diameter "d, wherein D>d). The reduced diameter "d" resulting from actuation of the internal actuatable collapsing mechanism (e.g., pulling on the pull wire 140 in a proximal direction) clamps or pinches down on the clot 200 captured therein tightening its grip thereby minimizing the risk of dislodgement during retrieval while navigating through the vasculature.

Figure 2B:
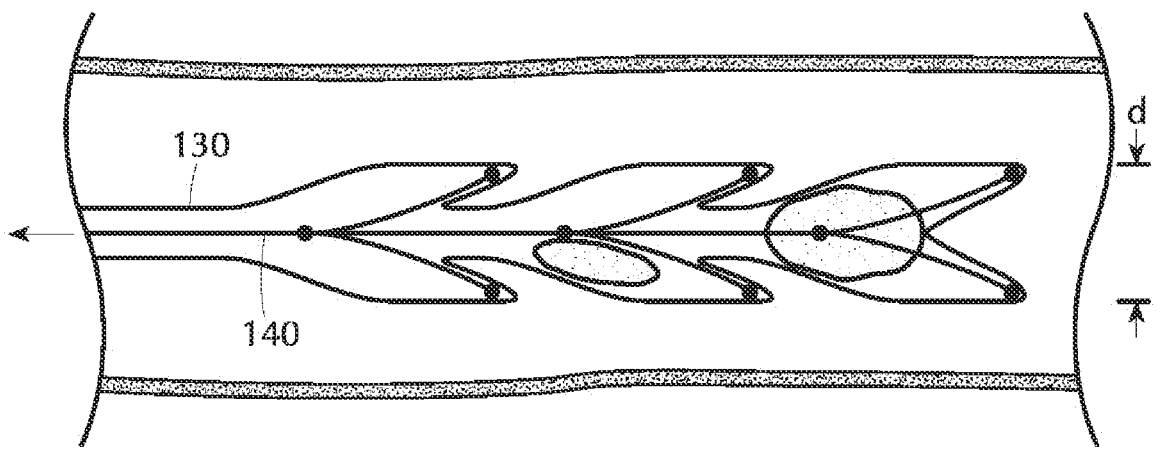
FIG. 2B is a side view of the exemplary mechanical thrombectomy device of FIG. 2A with the two clots embedded therein; wherein the mechanical thrombectomy device is depicted in a radially partially collapsed state (i.e., reduced in outer diameter/outer profile relative to that in the radially expanded state of FIG. 2A) clamping down on the two clots captured therein as a result of actuating the internal actuatable collapsing mechanism.
Figure 3A:
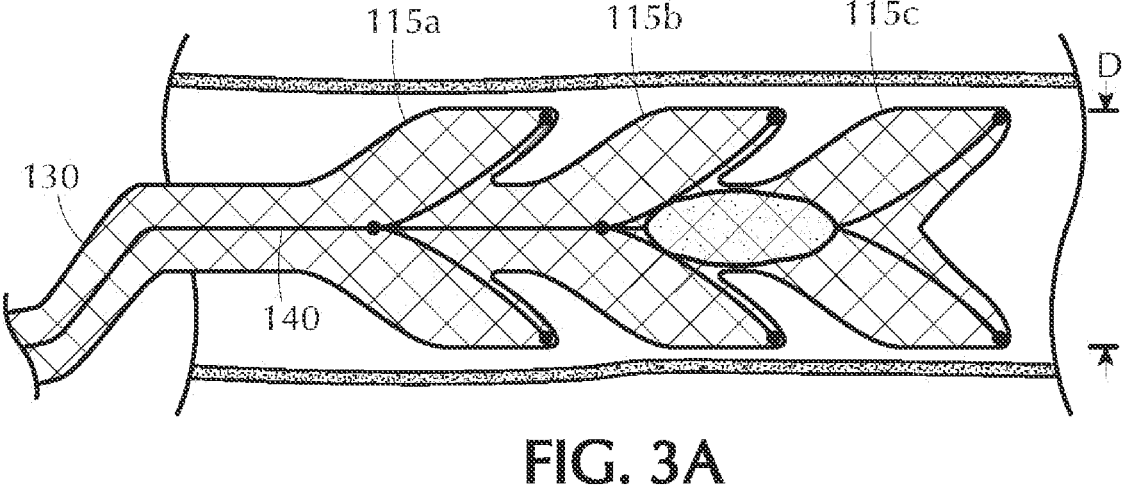
FIG. 3A is an enlarged side view of an exemplary mechanical thrombectomy device of FIG. 1A with a single clot captured therein; wherein the mechanical thrombectomy device is depicted in a radially expanded state prior to actuating the internal actuatable collapsing mechanism.
Figure 3B:
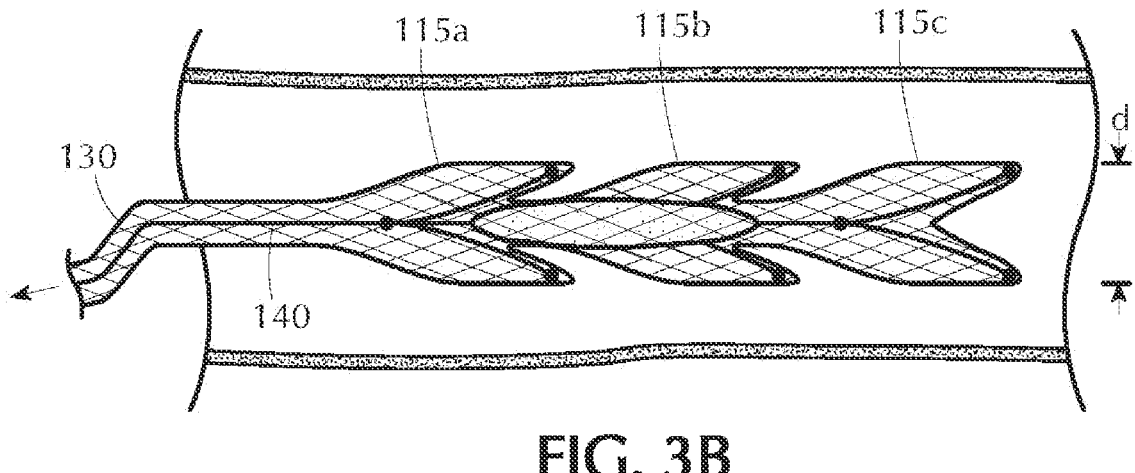
FIG. 3B is an enlarged side view of the exemplary mechanical thrombectomy device of FIG. 3A with a single clot captured therein; wherein the mechanical thrombectomy device is depicted in a radially partially collapsed state (i.e., reduced in outer diameter/outer profile relative to that of the radially expanded state in FIG. 3A) as a result of actuating the internal actuatable collapsing mechanism and clamping down on, gripping or pinching so as to physically compress (e.g., deform in shape) the captured clot therein.

Enlarged views of the example mechanical thrombectomy device of FIGS. 2A & 2B with only a single clot captured therein are depicted in FIGS. 3A & 3B, respectively, to illustrate the compression, squeezing or pinching of the captured clot when the internal actuatable collapsing mechanism is deployed. Prior to deployment of the internal actuatable collapsing mechanism, the mechanical thrombectomy device unsheathed from the microcatheter has an expanded outer profile or outer diameter "D". Once the clot is captured, in response to tension (i.e., pulling in a proximal direction) applied to the pull wire 140 the scaffolding sections 115*a*, 115*b*, 115*c* of the mechanical thrombectomy device 100 connected thereto partially collapse (i.e., reduce in outer diameter or outer profile "d" depicted in FIG. 3B, wherein d<D. The reduced outer diameter or outer profile "d" of the mechanical thrombectomy device in this radially partially collapsed state minimizes the friction force or drag imparted on the walls of the vessels during retrieval of the captured clot. In addition, the radially partial collapse of the mechanical thrombectomy device compresses, squeezes or pinches the captured clot therein tightening its grip thereby minimizing potential risk of dislodgement during retrieval. The enlarged view of FIG. 3B clearly shows the clenched radially partially collapsed cage structure of the mechanical thrombectomy device compressing (e.g., physically deforming or reshaping) the captured clot therein.

It is also noted that when the internal actuatable collapsing mechanism is deployed the radially partially collapsed mechanical thrombectomy device may have a smaller reduction in outer diameter in that scaffolding section in which a clot is captured relative to another scaffolding section that is free or devoid of any captured clot. FIG. 6A is a side view of the present inventive mechanical thrombectomy device with a clot capture therein prior to actuating the internal actuatable collapsing mechanism. After actuation of the internal actuatable collapsing mechanism, as depicted in FIG. 6B, that scaffolding section of the mechanical thrombectomy device having a capture clot therein undergoes a smaller reduction in outer diameter relative to those scaffolding section(s) of the mechanical thrombectomy device in which no clot is present.

Thus, while there have been shown, described, and pointed out fundamental novel features of the invention as applied to a preferred embodiment thereof, it will be understood that various omissions, substitutions, and changes in the form and details of the systems/devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A mechanical thrombectomy device comprising:
a self-expanding cage structure transitionable from a radially expanded state to a radially partially collapsed state of reduced outer diameter relative to that while in the radially expanded state; and
an internal actuatable collapsing mechanism fixedly attached internally to the self-expanding cage structure; wherein the internal actuatable collapsing mechanism when actuated imposes a radially inward tension on the self-expanding cage structure transitioning to the radially partially collapsed state;
wherein the internal actuatable collapsing mechanism is at least one pull wire including a main section and a plurality of branch sections with each branch section having a first end connected to the main section and an opposite second end fixedly connected internally to the self-expanding cage structure.

2. The mechanical thrombectomy device according to claim 1, wherein the main section and the plurality of branch sections comprising the at least one pull wire are formed from a single piece of wire or multiple wire sections fixedly secured together to form a single unit.

3. A mechanical thrombectomy device comprising:
a self-expanding cage structure transitionable from a radially expanded state to a radially partially collapsed state of reduced outer diameter relative to that while in the radially expanded state; and
an internal actuatable collapsing mechanism fixedly attached internally to the self-expanding cage structure; wherein the internal actuatable collapsing mechanism when actuated imposes a radially inward tension on the self-expanding cage structure transitioning to the radially partially collapsed state;
wherein the self-expanding cage structure comprises a plurality of articulated scaffolding sections; and the internal actuatable collapsing mechanism is at least one pull wire including a main section and a plurality of branch sections; each of the plurality of branch sections has a first end connected to the main section and an opposite second end fixedly connected internally to one of the plurality of articulated scaffolding sections.

4. The mechanical thrombectomy device according to claim 3, wherein every one of the plurality of articulated scaffolding sections has associated therewith one of the plurality of branch sections internally attached thereto.

5. The mechanical thrombectomy device according to claim 3, wherein the internal actuatable collapsing mechanism is a plurality of pull wires independently actuatable of each other; each of the plurality of pull wires is connected internally to a different one of the plurality of articulated scaffolding sections.

6. A mechanical thrombectomy device comprising:
a self-expanding cage structure transitionable from a radially expanded state to a radially partially collapsed state of reduced outer diameter relative to that while in the radially expanded state; and
an internal actuatable collapsing mechanism fixedly attached internally to the self-expanding cage structure; wherein the internal actuatable collapsing mechanism when actuated imposes a radially inward tension on the self-expanding cage structure transitioning to the radially partially collapsed state;
wherein the internal actuatable collapsing mechanism is a plurality of pull wires independently actuatable of each other; and wherein the self-expanding cage structure comprises a dual structure including an inner self-expanding cage structure disposed within an inner axial channel of an outermost self-expanding cage structure, wherein each self-expanding cage structure is independently deployable of one another; and the plurality of pull wires includes a first pull wire attached internally to the outermost self-expanding cage structure and a second pull wire attached internally to the inner self-expanding cage structure; wherein the first and second pull wires are actuatable independently of one another to radially partially collapse a respective one of the outermost self-expanding cage structure and/or inner self-expanding cage structure.

7. A method for capture and retrieval of an occlusion in a vessel using a mechanical thrombectomy device having a self-expanding cage structure transitionable from a radially expanded state to a radially partially collapsed state of reduced outer diameter relative to that while in the radially expanded state; and the mechanical thrombectomy device further including an internal actuatable collapsing mechanism fixedly attached internally to the self-expanding cage structure; and wherein the internal actuatable collapsing mechanism when actuated imposes a radially inward tension on the self-expanding cage structure transitioning to the radially partially collapsed state, the method comprising:
inserting a guidewire though the vessel to a proximal side of the occlusion;
tracking a microcatheter over the guidewire to the proximal side of the occlusion;
together or independently one-after-the other, advancing the guidewire and microcatheter through the occlusion;
withdrawing the guidewire from the vessel;

advancing the mechanical thrombectomy device through the microcatheter;

actuating the mechanical thrombectomy device thereby transitioning to the radially expanded state and capturing the occlusion therein;

actuating the internal actuatable collapsing mechanism imposing a radially inward tension internally within the self-expanding cage structure thereby transitioning from the radially expanded state to the radially partially collapsed state reduced in outer diameter while compressing the occlusion captured therein; and with the compressed occlusion captured therein, drawing back into the microcatheter the self-expanding cage structure while in in the radially partially collapsed state;

wherein the internal actuatable collapsing mechanism is at least one pull wire including a main section and a plurality of branch sections with each branch section having a first end connected to the main section and an opposite second end connected internally to the self-expanding cage structure.

8. The method according to claim 7, wherein the main section and the plurality of branch sections comprising the at least one pull wire are formed from a single piece of wire or multiple wire sections fixedly secured together to form a single unit.

9. A method for capture and retrieval of an occlusion in a vessel using a mechanical thrombectomy device having a self-expanding cage structure transitionable from a radially expanded state to a radially partially collapsed state of reduced outer diameter relative to that while in the radially expanded state; and the mechanical thrombectomy device further including an internal actuatable collapsing mechanism fixedly attached internally to the self-expanding cage structure; and wherein the internal actuatable collapsing mechanism when actuated imposes a radially inward tension on the self-expanding cage structure transitioning to the radially partially collapsed state, the method comprising:

inserting a guidewire though the vessel to a proximal side of the occlusion;

tracking a microcatheter over the guidewire to the proximal side of the occlusion;

together or independently one-after-the other, advancing the guidewire and microcatheter through the occlusion;

withdrawing the guidewire from the vessel;

advancing the mechanical thrombectomy device through the microcatheter;

actuating the mechanical thrombectomy device thereby transitioning to the radially expanded state and capturing the occlusion therein;

actuating the internal actuatable collapsing mechanism imposing a radially inward tension internally within the self-expanding cage structure thereby transitioning from the radially expanded state to the radially partially collapsed state reduced in outer diameter while compressing the occlusion captured therein; and with the compressed occlusion captured therein, drawing back into the microcatheter the self-expanding cage structure while in in the radially partially collapsed state;

wherein the self-expanding cage structure comprises a plurality of articulated scaffolding sections; and the internal actuatable collapsing mechanism is at least one pull wire including a main section and a plurality of branch sections; each of the plurality of branch sections has a first end connected to the main section and an opposite second end connected internally to one of the plurality of articulated scaffolding sections.

10. The method according to claim 9, wherein every one of the plurality of articulated scaffolding sections has associated therewith one of the plurality of branch sections internally attached thereto.

11. The method according to claim 9, wherein the internal actuatable collapsing mechanism is a plurality of pull wires independently actuatable of each other; each of the plurality of pull wires is connected internally to a different one of the plurality of articulated scaffolding sections.

12. The method according to claim 11, wherein actuating comprises independently controlling an amount of tension imposed in a proximal direction on each of the plurality of pull wires independently regulating an extent of reduction in the outer diameter when transitioned to the radially partially collapsed state for each one of the plurality of articulated scaffolding sections connected thereto.

13. A method for capture and retrieval of an occlusion in a vessel using a mechanical thrombectomy device having a self-expanding cage structure transitionable from a radially expanded state to a radially partially collapsed state of reduced outer diameter relative to that while in the radially expanded state; and the mechanical thrombectomy device further including an internal actuatable collapsing mechanism fixedly attached internally to the self-expanding cage structure; and wherein the internal actuatable collapsing mechanism when actuated imposes a radially inward tension on the self-expanding cage structure transitioning to the radially partially collapsed state, the method comprising:

inserting a guidewire though the vessel to a proximal side of the occlusion;

tracking a microcatheter over the guidewire to the proximal side of the occlusion;

together or independently one-after-the other, advancing the guidewire and microcatheter through the occlusion;

withdrawing the guidewire from the vessel;

advancing the mechanical thrombectomy device through the microcatheter;

actuating the mechanical thrombectomy device thereby transitioning to the radially expanded state and capturing the occlusion therein;

actuating the internal actuatable collapsing mechanism imposing a radially inward tension internally within the self-expanding cage structure thereby transitioning from the radially expanded state to the radially partially collapsed state reduced in outer diameter while compressing the occlusion captured therein; and with the compressed occlusion captured therein, drawing back into the microcatheter the self-expanding cage structure while in in the radially partially collapsed state;

wherein the self-expanding cage structure comprises a dual structure including an inner self-expanding cage structure disposed within an inner axial channel of an outermost self-expanding cage structure, wherein each self-expanding cage structure is independently deployable of one another; and the internal actuatable collapsing mechanism is a plurality of pull wires independently actuatable of each other and the plurality of pull wires includes a first pull wire attached internally to the outermost self-expanding cage structure and a second pull wire attached internally to the inner self-expanding cage structure; wherein the actuating step comprises independently pulling in a proximal direction the first and/or second pull wires respectively imposing internal tension within thereby transitioning to the radially partially collapsed state a respective one of the outermost self-expanding cage structure and/or inner self-expanding cage structure.

14. The method according to claim 13, wherein actuating further comprises independently controlling an amount of tension imposed in a proximal direction on each of the first and second pull wires independently regulating an extent of reduction in the outer diameter when transitioned to the radially partially collapsed state for each of the outermost self-expanding cage structure and/or the inner self-expanding cage structure connected thereto.

* * * * *